United States Patent [19]

Lee et al.

[11] 4,292,452

[45] Sep. 29, 1981

[54] RHODIUM-CATALYZED HYDROGENATION OF UNSATURATED ALDEHYDES TO UNSATURATED ALCOHOLS

[75] Inventors: Richard J. Lee, Downers Grove; Delbert H. Meyer, Naperville; Darrell M. Senneke, Aurora, all of Ill.

[73] Assignee: Standard Oil Company (Indiana), Chicago, Ill.

[21] Appl. No.: 874,132

[22] Filed: Feb. 1, 1978

[51] Int. Cl.$^3$ .................... C07C 29/14; C07C 33/03
[52] U.S. Cl. ................ 568/881; 252/431 R; 252/431 N
[58] Field of Search .......................... 568/881

[56] References Cited

U.S. PATENT DOCUMENTS 4,072,720  2/1978  Haag et al. .................... 568/881

OTHER PUBLICATIONS

Mizoroki et al., "Bulletin of the Chemical Society of Japan", vol. 50(8), 2148-2152 (1977).
Haag et al., "Catalysis", vol. 1, 465-475 (1973).
Jurewicz et al., "Advances in Chemistry", Series No. 132, 240-251 (1974).

*Primary Examiner*—Joseph E. Evans
*Attorney, Agent, or Firm*—William H. Magidson; William T. McClain

[57] ABSTRACT

Process for selective hydrogenation of aliphatic unsaturated aldehyde to unsaturated alcohol with gaseous hydrogen using supported rhodium-complex catalyst.

This invention relates to a process for preparing unsaturated aliphatic alcohols wherein unsaturated aliphatic aldehydes are selectively hydrogenated using supported rhodium-complex catalyst.

Unsaturated alcohols have use in the production of plastics and perfumes. Crotonyl alcohol, for example, has utility for the production of copolymers with vinyl acetate or styrene, and also as an intermediate for synthesis of other organic compounds. Allyl alcohol is a precursor for butanediol which is used to produce tetrahydrofuran, polyesters such as polybutylene terephthalate, and polybutylene oxide based polyurethanes.

Particular difficulty in selectively hydrogenating alpha, beta unsaturated aldehydes is described in U.S. Pat. No. 3,655,777 (Rylander et al., 1972, assigned to Engelhard Minerals and Chemicals) wherein patentees teach many catalysts, e.g., palladium, platinum, rhodium, ruthenium, and nickel, usually reduce the double bond in preference over reduction of the carbonyl group. Rylander also teaches a high pressure process to obtain unsaturated alcohols using an osmium catalyst.

9 Claims, No Drawings

RHODIUM-CATALYZED HYDROGENATION OF UNSATURATED ALDEHYDES TO UNSATURATED ALCOHOLS

The commercial feasibility of these processes is dependent upon product yields and recovery of the expensive catalysts. U.S. Pat. No. 4,020,116 (Vanderspurt, 1977, assigned to Celanese) teaches a process for producing unsaturated alcohol from unsaturated aldehyde using a rhenium catalyst supported on controlled-pore-size glass, which facilitates catalyst recovery. Accordingly, there is a need for processes of converting unsaturated aldehydes to the corresponding unsaturated alcohols using supported catalysts.

The general object of this invention is to produce unsaturated alcohols from unsaturated aldehyde precursors, with the achievement of good yield and facile recovery of an effective catalyst. A particular object of this invention is to achieve selective hydrogenation of unsaturated aliphatic aldehydes to produce unsaturated aliphatic alcohols under mild conditions employing supported catalyst.

The objects of this invention can be attained by employing an active rhodium-complex catalyst anchored on a support, permitting convenient separation of the catalyst. The process of this invention has the advantage of operation under mild conditions with an effective, supported catalyst.

Briefly, our invention comprises selective hydrogenation of aliphatic unsaturated aldehydes to produce the corresponding unsaturated alcohols employing gaseous hydrogen reactant in the presence of supported rhodium-complex catalyst. The supports for the rhodium-complex catalyst of this invention facilitate convenient rhodium recovery. Our invention is particularly surprising since, while Mizoroki et al. report in the Bulletin of the Chemical Society of Japan, vol. 50 (8) 2148–2152 (1977), which is incorporated herein by reference, that rhodium-complexes were found to be effective in catalyzing selective hydrogenation of cinnamaldehyde to cinnamyl alcohol in the presence of strongly basic amines, such as triethylamine or N-methylpyrrolidine under oxo-reaction conditions. These investigators reported that in the case of aliphatic unsaturated aldehydes such as croton aldehyde, 2-hexenal and 2-ethyl-2-hexenal, only saturated alcohols were produced under the same reaction conditions as those used to produce the unsaturated cinnamyl alcohol from cinnamaldehyde. When Mizoroki et al. attempted to selectively hydrogenate acrylaldehyde (acrolein), no allyl alcohol was produced and only propionaldehyde was produced in trace amounts. These investigators further report that a supported rhodium-complex catalyzed the selective hydrogenation of cinnamaldehyde to cinnamyl alcohol under oxo-reaction conditions; however, neither hydrogenation of aliphatic unsaturated aldehydes using the supported rhodium catalyst was reported nor was improved selectivity suggested. We have demonstrated in work done prior to the publication of Mizoroki et al. that aliphatic unsaturated aldehydes can be successfully hydrogenated with good selectivity to the unsaturated alcohol using supported rhodium-complex catalyst under both oxo-reaction conditions and under reaction with hydrogen alone.

The support for the rhodium-complex catalysts of this invention facilitates convenient rhodium recovery. Suitable supports for the rhodium-complex catalysts of this invention include polymers having functional phosphorous, nitrogen, or sulfur atoms available to effect ligand coordination with rhodium. Specifically, useful pendant groups include $-P(C_xH_y)_2$, $-CH_2-P\phi_2$, $-N(CH_3)_2$, $-CH_2-N(CH_3)_2$, and $-SH$. For example, any of the supports disclosed by Haag et al. in CATALYSIS vol. 1, 465–475, Elsevier (1973) and Jurewicz et al., Advances in Chemistry Series No. 132: 240–251 (1974), which are incorporated herein by reference, can be used. Haag et al. describe some of the coordinating organic polymers which have been used for rhodium-complex catalyst preparation; functional pendant groups are usually chemically incorporated by attachment, for example: tertiary amines, tertiary phosphines and thiols.

Jurewicz et al. disclose the use of polypyridine, polyvinylpyridine, and aminated derivatives of polystyrene and styrene copolymers including poly(N,N-dimethylbenzylamine), poly(N,N-dimethylaniline) and poly(1-phenyl-2-N,N-dimethylaminoethane). Aminated, porous styrene-divinylbenzene copolymers, crosslinked with divinylbenzene to varying degrees in the molar range 1–40% of the monomer reacted, commercially available from Rohm and Haas under the registered tradename Amberlyst$^{(R)}$ for anion exchange resins, are particularly useful. These resins can be prepared by the methods taught in U.S. Pat. No. 2,591,574 (McBurney, 1952) assigned to Rohm and Haas Company, which is incorporated herein by reference. Generally, preparation of these resins involves a three step process: 60% to 99.9% styrene, on a molar basis, is polymerized with 0.1% to 40% divinylbenzene; the resulting crosslinked polymer is chloromethylated using chloromethyl ether in order to obtain chloromethyl groups on the benzene rings; the chloromethylated resin is then aminated, for example by reacting dimethylamine in order to obtain tertiary amine groups on the polymer in the form N,N-dimethylbenzylamine, which tertiary amine groups are available for further complexation. Amberlyst A21, crosslinked using divinylbenzene in the nominal amount of about 17 molar percent, is a particularly useful support for the rhodium-complex catalyzed process of this invention because of its porous, insoluble bead structure. Amberlyst A21 beads contain nitrogen between about 4.2 and about 4.8 mequiv./gram resin, in the form of tertiary N,N-dimethylbenzylamine.

The source of rhodium in the supported complex can be from compounds such as $RhCl_3$, $Rh_4(CO)_{12}$, $Rh_6(CO)_{16}$, $Rh_2Cl_2(CO)_4$, and like compounds wherein the rhodium is "anchored" to the polymer by ligand exchange or bridge splitting reactions.

The supported rhodium complex catalyst of this invention can be prepared by reacting the functionalized support with the rhodium compound, preferably in the presence of ligands which can activate the resulting coordination complex. Such activating ligands include carbon monoxide, nitriles, olefins and cycloolefins. The catalyst complex can be prepared apart from the selective hydrogenation process or under in situ conditions. For example, the catalyst complex can be prepared in a nitrogen-purged autoclave by adding support and rhodium compound together with alcohol or ether reaction medium such as ethanol, methanol, dioxane and tetrahydrofuran. Preferably, aromatic nitrile is added and the autoclave is pressured with carbon monoxide to about 800–1500 psig. The autoclave is then heated and maintained at between about 30°–100° C. until the reaction is terminated. After cooling, the resin particles are removed and washed.

Hydrogen-containing gas, reacted with unsaturated aldehyde in the process of this invention, can contain a minor amount of inert gas; however, when hydroformylation gas is used, the molar ratio of hydrogen to carbon monoxide can range from about 1:3 to 10:1.

While generally any unsaturated aliphatic aldehyde can be selectively hydrogenated to the corresponding unsaturated alcohol in good yield using the process of this invention, the alpha, beta-unsaturated aldehydes comprise a preferred class of reactants; representative are acrolein, methacrolein, crotonaldehyde, tiglic aldehyde, alpha-ethyl acrolein, beta-methyl crotonaldehyde, alpha, beta-dimethyl crotonaldehyde, beta-ethyl crotonaldehyde, alpha-methyl-beta-isopropyl acrolein, alpha-pentyl-beta-propyl acrolein, and 2-hexenal.

The selective hydrogenation reactions can be carried out at pressures in the range 10–1000 psig and temperatures in the range 0° C.–250° C.; mild conditions of about 80–100 psig and 20° C.–100° C. are preferred. The reactions can be carried out batchwise or continuously in any suitable reactor including a simple low pressure reactor. In a batch reaction, for example, the selective hydrogenation is carried out in a reactor similar to a Fisher-Porter pressure bottle; the supported rhodium-complex catalyst is added to the purged bottle and the unsaturated aldehyde, typically acrolein, is added to the catalyst neat or in a solution with alcohol or cyclic ether. The supported rhodium-complex catalyst can be used in molar ratio of rhodium to unsaturated aldehyde charged in the range of about $1\times10^{-4}:1$ to about $1\times10^{-10}:1$. The reactor is then pressured and maintained at about 80 psig with hydrogen; the reaction temperature can be held at about 25° C. to produce unsaturated alcohol in good yield.

In contrast to conventional homogeneous $RhCl(P\phi_3)_3$, which has been used to selectively hydrogenate the double bond in unsaturated aldehydes to produce saturated aldehydes as described in *Homogeneous Hydrogenation*, B. L. James, John Wiley and Sons, 224–225 (1973), the process of this invention produces unsaturated alcohols from unsaturated aldehydes using supported rhodium-complex catalysts.

The following examples are illustrative of this invention but do not indicate limitation upon the scope of the claims.

EXAMPLE I

"In Situ" Preparation of Catalyst

Procedure: Two of the reagents used to prepare the catalyst were sequestered in a teflon pouch which is semi-permeable to solvents and reactants and products of the reaction. These two reagents were 0.3 g of rhodium chloride tri-hydrate (=0.0012 moles) of rhodium and 8.0 g of Amberlyst A21 beads (Rohm and Haas). The resin beads contained 0.038 moles of nitrogen atoms. The preparation began by suspending the teflon pouch inside a 300 ml stirred-autoclave, which had been purged with dry nitrogen; 21.56 g of acrolein (=0.3845 mole) and 79.14 g of methanol (=2.47 moles) were introduced. Immediately following the introduction of the reactants 5.05 g of benzonitrile (=0.0489 mole) were injected into the autoclave. The autoclave was purged with carbon monoxide gas and sealed. The autoclave was then pressured to 1200 psig with a (2:1) molar hydrogen/carbon monoxide mixture. Heat was applied through a heating mantle and controlled at 50.2° C. The reaction was allowed to run for a duration of three hours. Approximately half of the gas pressure was dissipated. A 1:1 molar ratio of hydrogen to carbon monoxide gas was then used to replenish the consumed gases and pressure was restored to 1200 psig. The reaction was continued for a total of 139 hours; then the catalyst beads were recovered from the pouch and washed with ethanol and dried. Rhodium analysis showed 1.40% rhodium (=0.0011 mole), virtually all the rhodium charged.

EXAMPLE II

Catalyst beads prepared as described in Example I containing 1.4647 grams of rhodium (0.0002 mole) were weighed into a Fisher-Porter pressure bottle pre-purged thoroughly with dry nitrogen. A solution of 0.154 mole of acrolein and 0.5986 mole of methanol were then added to the catalyst. The pressure bottle was then sealed and purged three times with CO. The reaction was carried out at 25° C. and 80 psig with a (1:1) molar mixture of hydrogen and carbon monoxide gases. After 50 hours, 89% of the acrolein had been converted to the following products based upon gas chromatographic analysis:

| | |
|---|---|
| 63.67% mol | allyl alcohol |
| 3.62% mol | propionaldehyde |
| 2.10% mol | propyl alcohol |
| 21.2% mol | hydroformylation products |

EXAMPLE III

Using only about half the amount of catalyst, containing 0.9387 grams of rhodium (0.00011 mole), the same procedure in Example II was repeated; however, the gas employed for reaction was pure hydrogen at 80 psig. After 162 hours, 3 times the reaction period of Example II, a 38.6% conversion of acrolein was achieved. The yield of allyl alcohol was measured to be 60% by chromatographic analysis; no detectable propyl alcohol or propionaldehyde was produced.

We claim:

1. A process for the selective hydrogenation of acrolein to allyl alcohol which comprises reacting acrolein with gaseous hydrogen at a temperature in the range 0° C.–250° C. in the presence of a rhodium-complex catalyst consisting essentially of:
   (a) a rhodium atom;
   (b) an organic polymer support having at least one functional atom selected from the group consisting of nitrogen and sulfur which is anchored onto the rhodium atom; and
   (c) a plurality of activating ligands coordinated with the rhodium atom.

2. The process of claim 1 wherein the temperature is within the range of about 20° C.–100° C.

3. The process of claim 1 wherein the gaseous hydrogen reactant consists essentially of hydrogen.

4. The process of claim 1 wherein the gaseous hydrogen reactant comprises a mixture of hydrogen and carbon monoxide.

5. The process of claim 1 wherein the activating ligands comprise an aromatic nitrile.

6. A process for the selective hydrogenation of acrolein to allyl alcohol which comprises reacting acrolein with gaseous hydrogen in the presence of a rhodium-complex catalyst anchored to an aminated organic polymer support at a temperature in the range 0° C.–250° C.

7. The process of claim 6 wherein the catalyst comprises the reaction product of a poly(N,N-dimethylbenzylamine) support with hydrated RhCl$_3$.

8. The process of claim 7 wherein the catalyst comprises the reaction product of an aromatic nitrile.

9. The process of claim 6 wherein the catalyst is prepared by reacting compositions comprising a rhodium compound, an aminated organic polymer support, carbon monoxide, hydrogen and acrolein.

* * * * *